United States Patent
Lachenbruch et al.

(10) Patent No.: US 6,699,266 B2
(45) Date of Patent: Mar. 2, 2004

(54) SUPPORT SURFACE WITH PHASE CHANGE MATERIAL OR HEAT TUBES

(76) Inventors: Charles A. Lachenbruch, 126 Linwood La., Summerville, SC (US) 29483; Richard I. Barnett, 921 Prince St., Georgetown, SC (US) 29440

( * ) Notice: Subject to any disclaimer, the term of this patent is extended or adjusted under 35 U.S.C. 154(b) by 7 days.

(21) Appl. No.: 10/012,772

(22) Filed: Dec. 8, 2001

(65) Prior Publication Data

US 2003/0109908 A1 Jun. 12, 2003

(51) Int. Cl.⁷ .................................. A61F 7/00
(52) U.S. Cl. ...................... 607/96; 607/108; 5/653
(58) Field of Search .................. 607/96, 104, 108–114; 606/20, 22; 5/421, 653

(56) References Cited

U.S. PATENT DOCUMENTS

| | | | |
|---|---|---|---|
| 3,313,405 A | | 4/1967 | Blackford |
| 4,391,267 A | * | 7/1983 | Arrhenius .................. 126/400 |
| 4,596,250 A | | 6/1986 | Beisang, III et al. |
| 4,651,369 A | | 3/1987 | Guldager |
| 4,671,267 A | | 6/1987 | Stout |

(List continued on next page.)

OTHER PUBLICATIONS

U.S. patent application Ser. No. 10/013,442, Lachenbruch et al., filed Dec. 8, 2001.
U.S. patent application Ser. No. 10/013,443, Lachenbruch et al., filed Dec. 8, 2001.
U.S. patent application Ser. No. 10/013,419, Lachenbruch et al., filed Dec. 8, 2001.

(List continued on next page.)

Primary Examiner—Roy D. Gibson
(74) Attorney, Agent, or Firm—Kathleen M. Harleston

(57) ABSTRACT

A support surface for general skin cooling, or reducing the incidence and promoting the healing of bedsores, includes:

(a) at least one thermal layer comprising: a phase change material having a melting point of between about 18 and 32 degrees Centigrade; a gel or viscous fluid carrier in which the phase change material is substantially evenly distributed; and a fluid-impermeable, conformable envelope surrounding the phase change material and the carrier;

(b) at least one conformable compression support layer beneath and adjacent to the thermal layer;

(c) at least one conformable base support layer beneath and adjacent to the compression layer, the base support layer having a higher indentor load deflection (ILD) than the compression layer. A preferred embodiment, with or without the thermal layer, includes a heat tube layer. Another preferred embodiment includes an envelope containing phase change material in a carrier material, without either of the support layers.

31 Claims, 9 Drawing Sheets

U.S. PATENT DOCUMENTS

| | | | | |
|---|---|---|---|---|
| 4,699,134 A | | 10/1987 | Samuelson | |
| 4,708,812 A | | 11/1987 | Hatfield | |
| 4,807,696 A | | 2/1989 | Colvin et al. | |
| 4,911,232 A | | 3/1990 | Colvin et al. | |
| 4,964,402 A | | 10/1990 | Grimm et al. | |
| 4,981,135 A | | 1/1991 | Hardy | |
| 4,999,867 A | | 3/1991 | Toivio et al. | |
| 5,010,608 A | | 4/1991 | Barnett et al. | |
| 5,033,136 A | | 7/1991 | Elkins | |
| 5,069,208 A | | 12/1991 | Noppel et al. | |
| 5,211,949 A | * | 5/1993 | Salyer | 424/402 |
| 5,290,904 A | | 3/1994 | Colvin et al. | |
| 5,300,103 A | | 4/1994 | Stempel et al. | |
| 5,334,646 A | | 8/1994 | Chen | |
| 5,366,801 A | | 11/1994 | Bryant et al. | |
| 5,456,852 A | * | 10/1995 | Isiguro | 252/70 |
| 5,486,207 A | * | 1/1996 | Mahawili | 607/104 |
| 5,511,260 A | | 4/1996 | Dinsmoor, III et al. | |
| 5,575,815 A | | 11/1996 | Slepian et al. | |
| 5,586,346 A | | 12/1996 | Stacy et al. | |
| 5,702,375 A | | 12/1997 | Angelillio et al. | |
| 5,713,143 A | | 2/1998 | Kendall | |
| 5,722,482 A | | 3/1998 | Buckley | |
| 5,800,480 A | | 9/1998 | Augustine et al. | |
| 5,817,145 A | | 10/1998 | Augustine et al. | |
| 5,837,002 A | | 11/1998 | Augustine et al. | |
| 5,887,437 A | | 3/1999 | Maxim | |
| 5,890,245 A | | 4/1999 | Klearman et al. | |
| 5,926,884 A | | 7/1999 | Biggie et al. | |
| 5,964,723 A | | 10/1999 | Augustine | |
| 5,983,429 A | | 11/1999 | Stacy et al. | |
| 5,984,953 A | | 11/1999 | Sabin et al. | |
| 6,004,662 A | | 12/1999 | Buckley | |
| 6,010,528 A | | 1/2000 | Augustine et al. | |
| 6,033,432 A | | 3/2000 | Augustine et al. | |
| 6,071,254 A | | 6/2000 | Augustine et al. | |
| 6,071,304 A | | 6/2000 | Augustine et al. | |
| 6,080,189 A | | 6/2000 | Augustine et al. | |
| 6,083,254 A | | 7/2000 | Evans | |
| 6,094,762 A | | 8/2000 | Viard et al. | |
| 6,095,992 A | | 8/2000 | Augustine | |
| 6,099,894 A | * | 8/2000 | Holman | 427/126.3 |
| 6,102,936 A | | 8/2000 | Augustine et al. | |
| 6,113,561 A | | 9/2000 | Augustine | |
| 6,119,474 A | | 9/2000 | Augustine et al. | |
| 6,120,530 A | | 9/2000 | Nuckols et al. | |
| 6,123,716 A | | 9/2000 | Augustine et al. | |
| 6,132,455 A | * | 10/2000 | Shang | 607/108 |
| 6,179,879 B1 | | 1/2001 | Robinson et al. | |
| 6,183,855 B1 | | 2/2001 | Buckley | |

OTHER PUBLICATIONS

Lon R. Horwitz, DPM, CWS; Thomas J. Burke, PHD; and Dale Carnegie, DPM, Augmentation of Wound Healing Using Monochromatic Infrared Energy, Advances in Wound Care, Jan./Feb. 1999, pp. 35–40, vol. 12 No. 1, Denver, Colorado, USA.

David P. Colvin, Enhanced Thermal Management Using Encapsulated Phase Change Materials an Overview, Advances in Heat and Mass Transfer in Biotechnology, ASME, 1999, HTD–vol. 363/BED–vol. 44, USA.

Mark E. Holman, The Use of Microencapsulated Phase–Change Materials to Enhance the Thermal Performance of Apparel, Advance in Heat and Mass Transfer in Biotechnology, 1999, pp. 235–239, HTD–vol. 363/BED–vol. 44 ASME, USA.

Perry S. Tepperman, MD, and Michael Devlin, MD, Therapeutic Heat and Cold, Postgraduate Medicine, Jan. 1983, pp. 69–76, vol. 73/No. 1, USA.

Justus F. Lehmann, M.D., C. Gerald Warren, M.P.A., and Stewart M. Scham, M.D., Therapeutic Heat and Cold, Clinical Orthopaedics and Related Research, pp. 207–245, USA.

Michael Sawyer, P.T., and Candise K. Zbieranek, P.T., The Treatment of Soft Tissue After Spinal Injury, Clinics in Sports Medicine, Apr. 1986, pp. 387–405, vol. 5, No. 2, Long Beach, California, USA.

Linda J. Hayes, Fabric With Micro Encapsulated Phase Change, Advances in Bioheat and Mass Transfer: Microscale Analysis of Thermal Injury Processes Instrumentation, Modeling, and Clinical Application, ASME, 1993, pp. 47–52, HTD–vol. 268, USA.

Phase–Change Heat–Storage Module, NASA Tech Briefs, Apr. 1989, p. 103, USA.

J. C. Mulligan, D. P. Colvin and Y. G. Bryant, Use of Two–Component Fluids of Microencapsulated Phase–Change Materials for Heat Transfer in Spacecraft Thermal Systems, Jun. 20–23, 1994, pp. 1–10, AIAA 94–2004, American Institute of Aeronautics and Astronautics, Washington, DC, USA.

D. P. Colvin, J. C. Mulligan, and Y. G. Bryant, Enhanced Heat Transport in Environmental Systems Using Microencapsulated Phase Change Materials, Jul. 13–16, 1992, 921224, SAE The Engineering Society for Advancing Mobility Land Sea Air and Space International, Warrendale, PA, USA.

Flam, E., Isayeva, E., Kipervas, Y., Shklyarevsky, V., and Raab, L. (1995). Skin Temperature and Moisture Management with a Low Air–Loss Surface. Ostomy Wound Management 41(9).

Kloth, L.C., Berman, J.E., Minkel, S., Sutton, C.H., Papanek, P.E., and Wurzel, J. (2000). Effects of Normothermic Dressing on Pressure Ulcer Healing. Advances in Skin & Wound Care, 13(2).

Price, P., Bale, S., Cook, H., and Harding, K.G. (2000). The Effect of a Radiant Heat Dressing on Pressure Ulcers. J. Wound Care, 9(4).

Microencapsulated Phase–Change Materials for Storage of Heat, NASA Tech Briefs, Jul. 1989, USA.

Santilli, S.M., MD, Ph.D., Valusek, B.A., Robinson C., BSN, RN, CVN, Use of a Noncontact Radiant Heat Bandage for the Treatment of Chronic Venous Stasis Ulcers. Advances in Wound Care, Mar. 1999, 13(2).

\* cited by examiner

SUPPORT SURFACE WITH PHASE CHANGE MATERIAL OR HEAT TUBES

BACKGROUND OF THE INVENTION

1. Technical Field

The present device is a support surface with a layer of heat tubes, and/or an upper thermal layer comprising a gel or viscous fluid carrier and phase change material, which resist warming of the support surface, and reduce the likelihood of ulceration and/or promote the healing of bedsores.

2. Background Information

Bedsores, or decubitus ulcers, can be a serious problem in bedridden or wheelchair-bound patients, particularly for people who are paralyzed, emaciated, post-surgical, elderly, emaciated, or diabetic. Bedsores are a common and persistent problem for those who have to spend a great deal of time in bed, and for their physicians and nurses. As baby boomers age, the elderly population increases, and the ordinary bedsore becomes more of a problem. People with casts or splints can also develop bedsores. Bedsores can penetrate to the muscles and bone and are surprisingly life-threatening on occasion. Where, for example, a geriatric patient in a fetal position develops bedsores between his knees, one or more of the bedsores can become gangrenous and necessitate amputation of a limb. A bedsore can progress to necrosis, septic arthritis, pathologic fracture, and septicemia.

To avoid bedsores, nurses or nurse assistants turn patients at prescribed intervals, inspect their skin and apply creams, give massages and baths to patients, exercise limbs, and promptly change wet bed sheets and bedclothes. Patients are placed on air-filled mattresses, sponge rubber "egg crate" mattresses, silicone gel or water mattresses, mattresses filled with fluid or tiny spheres, or Stryker turning mattresses. Protective padding, such as sheepskin or pillows, is placed on bony prominences under braces, casts, etc. Topical ointments, dressings, debridement, and antibiotics are prescribed to curb infections in decubitus ulcers. Prevention and management of bedsores is nevertheless difficult, and further assistance is needed.

Bedsores are ordinarily developed over the bony prominences of the body, such as the heels, sacrum (tailbone), ischia, greater trochanters, and ankles (external malleoli). It has been found that bedsores are less likely to form where the skin above the bony prominences is maintained at a slightly cooler temperature than normal skin temperature. The normal core temperature ("normothermia") of the human body is between 36° and 38° C. Skin temperature typically ranges between about 32° C. and about 38° C., depending on ambient temperature, the amount and type of clothing being worn, the core temperature, and where the skin is located on the body. On a typical mattress, seat cushion, inside a prosthesis, etc., heat is trapped between the body and the covered skin surface and the skin temperature rises rapidly to and is maintained at between about 36 and 38 degrees C. It is believed that skin temperatures in this range promote soft tissue breakdown by increasing tissue metabolism, promoting local perspiration, which wets and weakens the stratum corneum (surface layer of the skin), and increasing friction and shear forces between the sweaty skin and the bedding and/or clothes between the skin and the support surface.

The support surface of the present invention focuses "relative cooling", or cooling of the skin relative to the temperatures the skin would reach on a conventional mattress, under the bony prominences, where bedsores are more likely to form. Relative cooling is accomplished in the present invention with an envelope containing phase change material distributed in a gel or viscous fluid carrier. Cooling is held to a narrow temperature range just below normal skin temperature, since cold temperatures are uncomfortable and undesirable, particularly where the patient is emaciated or otherwise infirm. The present invention both reduces the likelihood of bedsore formation, and aids in the healing of early stage bedsores that have already formed.

BRIEF SUMMARY OF THE INVENTION

A support surface herein for comfort, or reducing the incidence and promoting the healing of bedsores, includes:

(a) at least one thermal layer comprising: a phase change material having a melting point of between about 18 and 32 degrees Centigrade; a gel or viscous fluid carrier in which the phase change material is substantially evenly distributed; and a fluid-impermeable, conformable envelope surrounding the phase change material and the carrier;

(b) at least one conformable compression support layer beneath and adjacent to the thermal layer;

(c) at least one conformable base support layer beneath and adjacent to the compression layer, the base support layer having a higher ILD than the compression layer;

wherein the layers are joined within an outer covering.

The support surface can also be used simply for delaying warming of the surface of the skin in contact with the support surface. A support surface pad or the like herein includes:

(a) phase change material having a melting point of between about 18 and 32 degrees Centigrade;

(b) a gel or viscous fluid carrier in which the phase change material is substantially evenly distributed; and (c) a fluid-impermeable, conformable envelope surrounding the phase change material and the carrier.

This support surface, which is preferably a mattress, support pad, or seat cushion, includes phase change materials just beneath its upper surface. Phase change materials for use herein are preferably encapsulated, and have a phase change such that temperatures between 18° and 33° C. will be delivered to the skin. A preferred embodiment of the support surface includes a heat tube layer for channeling heat from the warmer areas of the support surface to the cooler areas, or from the warmer areas of the body to the cooler skin regions, such as the extremities (e.g., ankles and heels). By maintaining the skin temperature below the levels typically recorded on a conventional foam mattress, the body is kept more comfortable, and the risk of developing bedsores and the like is greatly reduced. This inexpensive, easy to use support surface maintains a temperature within a prescribed range for a sufficient period of time to reduce the likelihood of ulceration and promote healing, when used in the prescribed manner.

A support surface herein alternatively includes:

(a) at least one heat tube layer comprising at least two adjacent heat tubes, at least one of the heat tubes containing a refrigerant liquid, the refrigerant liquid having a boiling point between about 80 and about 85 degrees Fahrenheit;

(b) at least one conformable compression support layer beneath and adjacent to the heat tube layer; and (c) at least one conformable base support layer beneath and adjacent to the compression layer, the base support layer having a higher ILD than the compression layer;

wherein the layers are joined within an outer covering.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein.

DETAILED DESCRIPTION OF THE INVENTION

Figure 1:
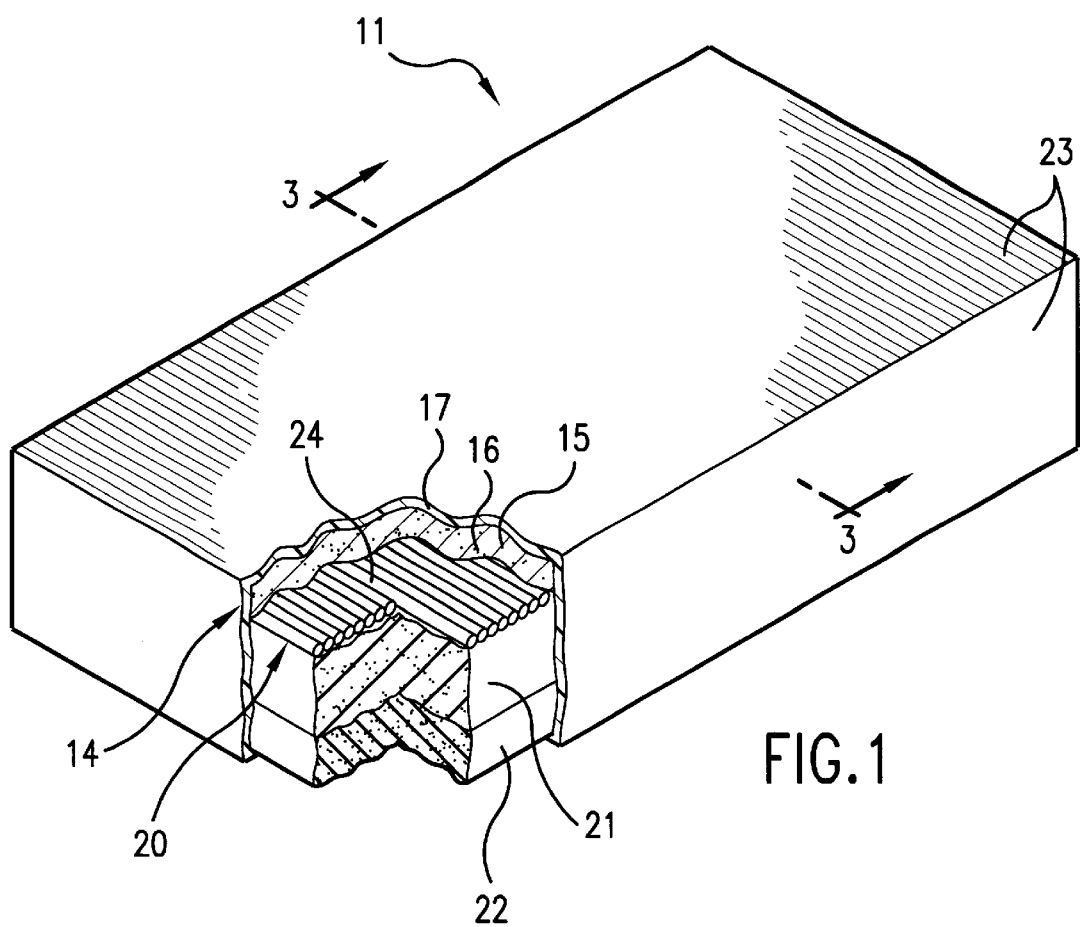
FIG. 1 shows a perspective view of a support mattress according to the present invention.

In the following description, like reference characters designate like or corresponding parts throughout the several views. Also, in the following description, it is to be understood that such terms as "front," "back," "within," and the like are words of convenience and are not to be construed as limiting terms. Referring in more detail to the drawings, the invention will now be described.

Turning first to FIG. 1, a support surface, generally referred to as 10, according to the present invention helps to reduce and promote the healing of bedsores (decubitus ulcers) and the like in persons using the support surface. This dual phase change clinical support surface 10 can be, for example, in the form of a mattress 11, or a support pad 12 placed over a conventional mattress or other sleeping, sitting, or resting surface, such as a seat cushion 13. It can also be in the form of a panel for insertion into a conventional mattress, or a small pad such as an operating room positioning pad, etc. Cooling pads are for placement between the knees of a patient lying on his side, or between the patient and the surface on which she is lying. Operating room positioning pads are small fluidic pads that can be placed wherever they are needed during surgery to reduce pressure points and hold the patient's body in place. These support surfaces 10 can be used in private homes, hospitals, clinics, long term care facilities, hospices, and the like.

As shown in the preferred embodiment of FIG. 1, the support surface 10, which is in the form of a bed mattress 11, includes a thermal layer 14 comprising phase change material (PCM) 15, which is indicated as dots in FIG. 1, relatively evenly distributed in a gel or viscous fluid carrier 16, which is indicated by hatching in FIG. 1. The PCM-containing carrier is enclosed by a relatively thin covering, or envelope 17. The support surface 10 preferably further comprises a heat tube, or pipe, layer 20 beneath the thermal layer 14. The support surface 10 also optionally includes a compression layer 21 beneath and adjacent to the heat tube layer 20, and a foam-like base layer 22 beneath and adjacent to the compression layer 21 or the heat tube layer 20. The compression layer 21 is substantially comprised of a low ILD (indentor load deflection, a measurement of foam rigidity) foam or the like, and the base layer 22 is substantially comprised of a higher ILD, or more rigid, foam, or a similar type of material. An outer covering 23, such as mattress ticking, preferably covers the top, bottom and sides of the mattress 11, and encloses the layers.

Thus, this preferred embodiment of a clinical support surface for reducing the incidence and promoting the healing of bedsores includes:

(a) at least one thermal layer 14 comprising: a phase change material 15 having a melting point of between about 18 and 32 degrees Centigrade; a gel or viscous fluid carrier 16 in which the phase change material 15 is substantially evenly distributed; and a fluid-impermeable, conformable envelope 17 surrounding the phase change material 15 and the carrier 16;

(b) at least one conformable compression support layer 21 beneath and adjacent to the thermal layer 14;

(c) at least one conformable base support layer 22 beneath and adjacent to the compression layer 21, the base support layer 22 having a higher indentor load deflection (ILD) than the compression layer 21;

wherein the layers 15, 21, 22 are joined within an outer covering 23.

Suitable phase change materials for use herein include C16 to C19 alkanes (i.e., alkanes with between about 16 and 19 carbons), and mixtures thereof. Preferred alkanes for use herein, then, are hexadecane (C16), heptadecane (C17), octadecane (C18), and nonadecane (C19). Alkanes may also be selected and mixed based on budget constraints, since some of them are much more expensive than others. The alkanes used in this invention can also be varied according to the degree of cooling desired for the particular part of the body that rests on that area of the support surface. Alkanes (or combinations thereof) may be selected according to the degree of cooling necessary to achieve the desired cooling effect. Warmer areas of the body, such as the sacrum, trunk, and generally proximal regions, may require more cooling, and hence higher PCM concentrations, than cooler, distal regions of the body, such as the ankles and heels, which may require little or no cooling.

The type of phase change material utilized herein can be varied according to budget, temperature requirements, and length of time that cooling is desired. Preferably, the phase change materials used herein melt at a temperature of between about 18 and 32 degrees Centigrade, more preferably between about 25 and 29 degrees Centigrade. When a person sits or lies on a support surface, his or her body heat begins to warm the support surface. Phase change materials cause the surface to resist that warming. On a conventional support surface, the heat given off from the skin is trapped in the generally insulative surface construction materials, such as foam. As a result, the support surface, and the skin with which it is in contact, warms nearly to core body temperature, often within about 60 and 90 minutes. In the case of the present support surface 10, the body warms the upper surface material, which warms the envelope beneath it, which warms the carrier, which transmits heat to the phase change material. Once the heat is conducted into the support surface from the skin, the thermal behavior departs from that of a conventional mattress because the heat that is conducted into the phase change material from the surrounding carrier is absorbed with no increase in temperature. It is believed that this energy is absorbed as latent heat in the phase change material's solid to liquid transition; that is, it goes into melting a fraction of the phase change material. As a result, the phase change material stays cooler at approximately the temperature of the phase transition, as does the surrounding carrier, envelope and skin.

Phase change materials are normally classified according to their melting points. Since most phase change materials have not been purified, they melt over a range of one or two degrees of temperature. When they are warmed to a temperature within this temperature range, the bulk of the phase change materials within the phase change material mixture will melt from a solid to a liquid. Many variables contribute to the performance of the support surface 10, including, but not limited to: 1) the type of phase change material and carrier; 2) the mixture of the two; 3) whether the phase change material is encapsulated; 4) the ambient temperature; 5) the rate at which heat is transported from the region directly under the patient to the edges of the support surface; 6) the size and body temperature of the particular patient laying or sitting on the support surface; and 7) how long the patient has been laying or sitting on the support surface. The phase change temperature, or melting point, of the phase change material distributed in the support surface is selected so that it is a few degrees cooler than the temperature that will actually be imparted to the body because it must remain cooler than the skin surface in order to draw heat from the skin. Although mattresses 11 and mattress pads 12 herein are designed for an average height and body shape, the design is versatile enough so that it may be custom designed to suit tall or short people, small or large sized people, etc.

The caregiver need not be concerned that the product will be so cold that it will harm the patient. The melting point of the phase change material is quite specific and reliable. The type of phase change material and the number and type of layers beneath are selected to ensure that the temperature that reaches the skin is one that is not harmful, and in fact is known to convey a therapeutic benefit.

The phase change material 15 is preferably microencapsulated so that it remains evenly distributed throughout the carrier even after repeated cycles of cooling and warming. The distribution of the phase change material into small, generally spherical capsules with a diameter of between about one and 100 microns significantly enhances heat transfer between the surrounding medium and the phase change material. Microencapsulation also prevents interaction, chemical or otherwise, over time between the phase change material and the carrier, or envelope, material, thus increasing product longevity. It also ensures pad conformability, which would not be the case if the pad were composed of pure alkane (physically resembles candle wax) in the solid state. Any suitable method for encapsulating the phase change material in a protective coating can be utilized. Powdered phase change material is preferably used because it is believed to enhance heat transfer due to its higher surface area.

The phase change materials are preferably microencapsulated in a thin coating, more preferably a polymer. The coating preferably forms a generally spherical shell around the phase change material with a shell thickness of between about 0.003 and two microns, most preferably between about 0.03 and about 0.05 micron thick.

The present invention does not require electricity, and does not include a power source or microprocessor. Cooling is automatic in the present invention; the present support surface does not require a manually operated temperature control unit.

Figure 2:
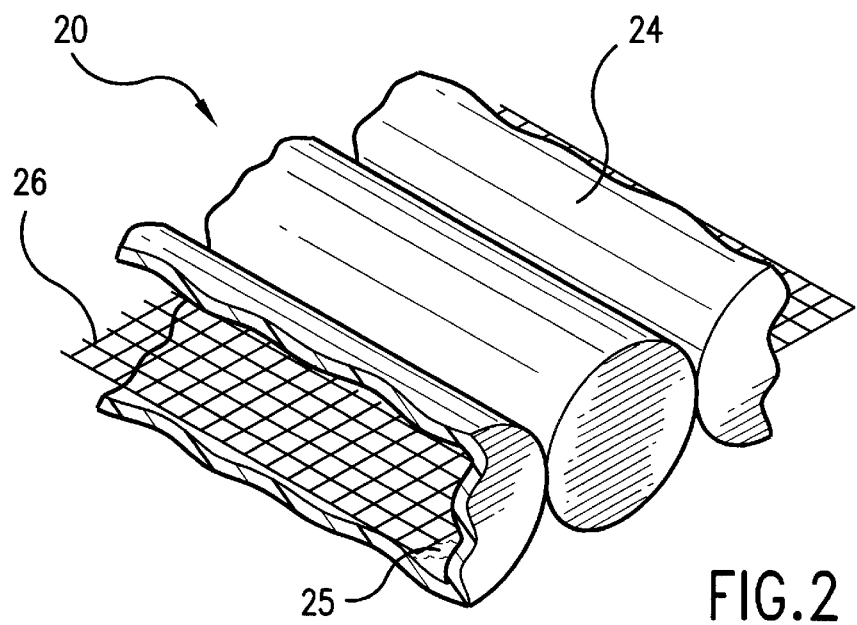
FIG. 2 is a partial cut-away perspective view of a support surface according to the present invention.

FIG. 2 shows several adjacent cylindrical heat tubes 24 in the heat tube layer 20 of the mattress 11 illustrated in FIG. 1. The heat tube layer 20 lies under the thermal layer 14. The heat tubes are preferably the same length as each other and are parallel to one another and connected together side by side. In FIG. 1, the heat tube layer 20 extends the width and length of the mattress 11. At least one (preferably all) hollow heat tube 24 holds a small amount of a refrigerant liquid 25, such as hydrofluoroethane, with a boiling point lower than average body temperature and greater than an average room temperature, or between about 23 and 33 degrees Centigrade. The heat tube liquid 25 condenses at a lower temperature than average body temperature. Sufficient space is left in each heat tube for expansion of the refrigerant liquid. The heat tube layer is enclosed, so that the refrigerant does not escape. If a small amount of refrigerant 25 does escape from the heat tube layer over time, it can be periodically serviced and recharged.

Preferred refrigerants include pentafluoropropane, fluorochemical liquid, or a mixture thereof. A most preferred mixture comprises from about 5 to 50 weight % 1,1,1,3,3-pentafluoropropane, and from about 50 to 95 weight % of a fluorochemical liquid. A preferred mixture has a boiling point between about 80 and 85 degrees Fahrenheit.

The heat tubes are made of a flexible material, so that they are comfortable to sit or lie on. The heat tube material must be strong and able to contain the refrigerant and withstand the liquid to gas cycling over time. The heat tubes are preferably substantially made of a gas impermeable film.

Another prominent ingredient in each heat tube is a thin, three-dimensional floating net 26, which preferably extends the length and width of the heat tube 24. The net 26 has small squares, which help to keep the heat tubes open despite pressure from the body or other weight on the support surface. The nets also help to distribute the liquid 25 evenly in the heat tube 24. A helical spring type net or tubular net is preferred. The size of the spacing between the net strands is dictated in part by the diameter of the heat tube. Preferably, the heat tubes 24 are made of vinyl, rubber, plastic, urethane, or an elastic polymer.

Figure 3:
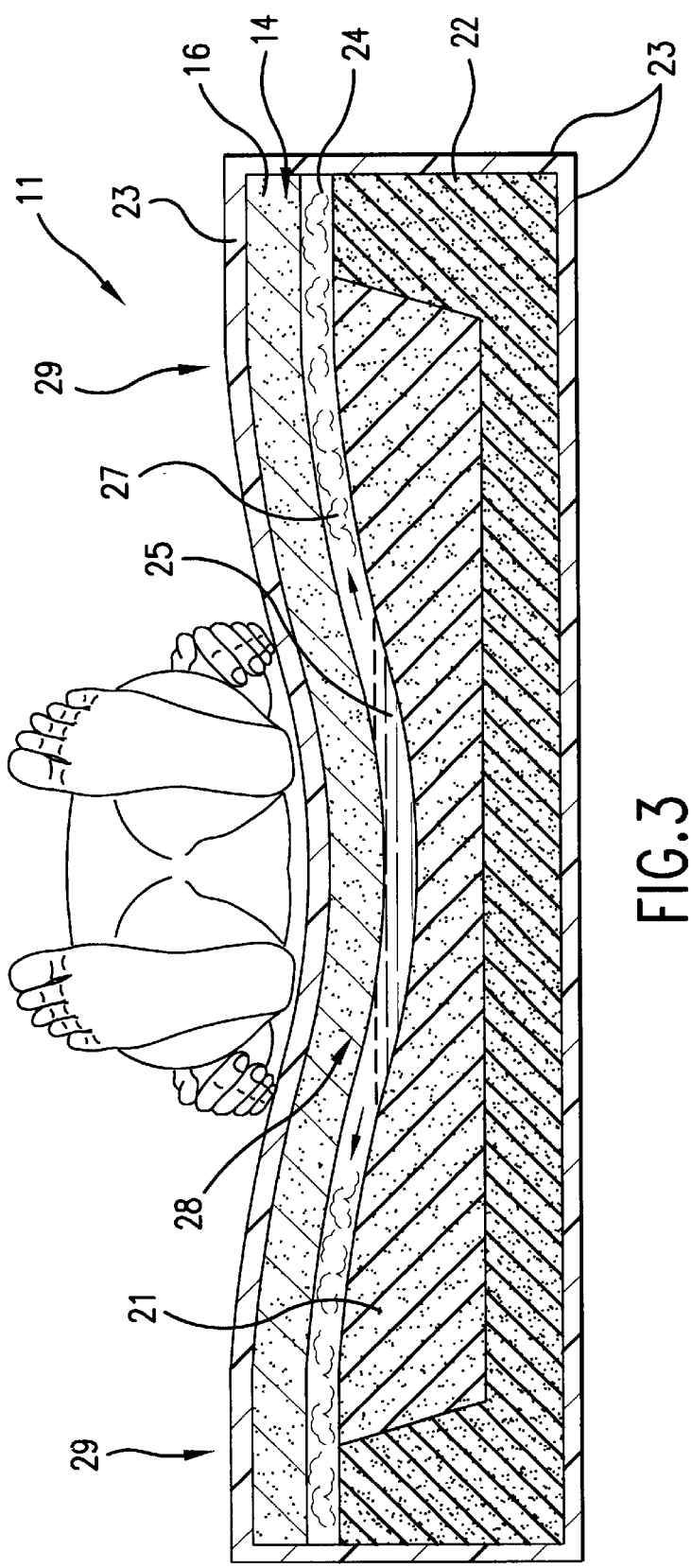
FIG. 3 is a cross-sectional view of the mattress of FIG. 1, taken along line 3—3.

In the preferred embodiment shown in FIGS. 1 and 3, mattress ticking 23 covers the top, bottom and sides of the mattress 11. In order from the top of the mattress 11 to the bottom in FIG. 3, the layers are as follows: thermal layer 14, heat tube layer 20, compression support layer 21, and the base support layer 22.

As shown in FIGS. 1 and 3, the heat tube layer 20 lies on a soft, conformable, compression support layer 21. This compression layer 21 is preferably made of a foam, or any other suitable insulative, comfortable, absorbent, conformable material, which provides cushioning and softness. The compression layer 21 may be thin or thick. The primary functions of the compression layer 21 are to support the user comfortably over time, keep the temperatures cool in the thermal layer 14, and to allow the mattress 11 to be compressed downward by the body, so that the condensed refrigerant 25 will gravitate toward the compressed area. This compressed area is thus not pre-ordained; it is wherever the body or bodies are on the support surface. Since different people like to sleep in different places on the bed, this is a useful feature of a mattress. The user(s) customizes his own mattress. This invention will convey its advantages no matter where the user has chosen to lie on it.

FIG. 3 illustrates the functioning of the compression layer 21 and the base support layer 22, and the heat tubes 24. In regard to the former, the more rigid base support layer 22 extends up on the left and the right sides of the mattress 11, as shown in FIG. 3. This has the effect of deterring the user's body from rolling out of the bed, and creating a gravitational sink along the longitudinal centerline of the bed, which cradles the body, as shown in FIG. 3. The user's body sinks down into the softer compression layer 21 at the center of the mattress 11. The compression layer 21 also tends to keep the sides of the bed, where the refrigerant vapor condenses, elevated relative to the center area. This encourages liquid refrigerant 25 to flow back to the center area of the mattress 11 from the sides.

In regard to heat tube functioning when the mattress 11 is in use, the parts of the warm body where it contacts the mattress surface heat the phase change material 15 distributed in the thick carrier 16 in the thermal layer 14. When the phase change material 15 in the preferred microcapsules reaches its melting point, it melts from a solid into a liquid. The phase change material slows heating of the mattress surface, so the user remains cooler for a longer period (versus lying on a conventional mattress). When the user leaves the bed, the temperature of the air close to the mattress 11 drops back to room temperature, which is virtuall always below the PCM melting point, and the majority of the phase change material 15 inside the microcapsules returns to its solid state. The mattress or other support surface is durable and the phase change material continues to cycle between its solid and liquid states through many uses over many years.

Meanwhile, as shown in FIG. 3, the refrigerant liquid 25 in the heating tubes 24 under the body is quickly heated by body heat to its relatively low boiling point. This area under the body is called here the "warm zone" 28. Where the support surface includes a heat tube layer, the compression layer 21 ensures depression of the reservoir of refrigerant 25 relative to the edges of the support surface. A single heat tube 24 is shown bisected in FIG. 3. The heat tube liquid 25 then converts to a vapor, or gas 27, inside the heat tube 24. The vapor 27 expands toward the "cool zone" 29, as indicated by the horizontal arrows in FIG. 3. The "cool zone" 29 here is the area of the mattress 11 that is not heated by the body, generally the right and left side areas of the mattress. As the vapor 27 expands toward the cool zone 29, it condenses and rejects the heat of fusion to the heat sink at the periphery. The refrigerant liquid 25 then flows back to the warm zone 28 for a second cycle of heating and cooling. This has the effect of keeping the area under the body cool. The body parts, such as the bony prominences, that sink more deeply into the central sink have greater surface area in contact with the mattress 11 and therefore are more exposed to the cooler temperature. The special mattress 11 construction allows the cool zone 29 to be elevated above the warm zone 28. This means that gravity encourages the flow of the condensed refrigerant liquid 25 back to the region that needs cooling, which is along the centerline of the mattress. Other embodiments of the present invention may also include a heat tube layer 24.

The present invention includes a clinical support surface for reducing the incidence and promoting the healing of bedsores with the heat tube layer, but without the phase change material and carrier. This embodiment of the support surface includes:

(a) at least one heat tube layer 20 comprising at least two adjacent heat tubes 24, at least one of the heat tubes 24 containing a refrigerant liquid 25, the liquid having a boiling point between about 80 and about 85 degrees Fahrenheit;
(b) at least one conformable compression support layer 21 beneath and adjacent to the heat tube layer 20; and
(c) at least one conformable base support layer 22 beneath and adjacent to the compression layer 21, the base support layer having a higher indentor load deflection (ILD) than the compression layer 21; wherein the layers 20, 21, 22 are joined within an outer covering.

The refrigerant liquid 25 is more preferably a pentafluoropropane, fluorochemical liquid, or a mixture thereof. The support surface is preferably a seat cushion 13, more preferably a wheelchair or day bed cushion. The cushion of the present invention is more comfortable than a conventional cushion, and the wheelchair occupant is less likely to develop bedsores. If the user does develop a decubitus ulcer on his or her bottom, the ulcer is less likely to worsen if the occupant uses a cooling seat cushion according to the present invention.

Figure 4:
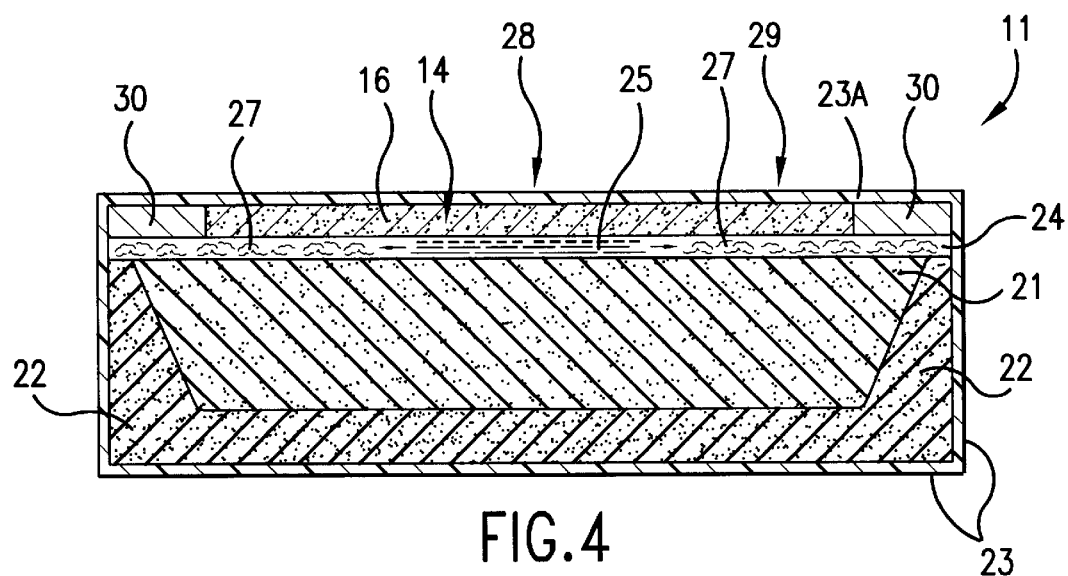
FIG. 4 is a cross-sectional view of an alternate embodiment of a support surface according to the present invention.
Figure 5:
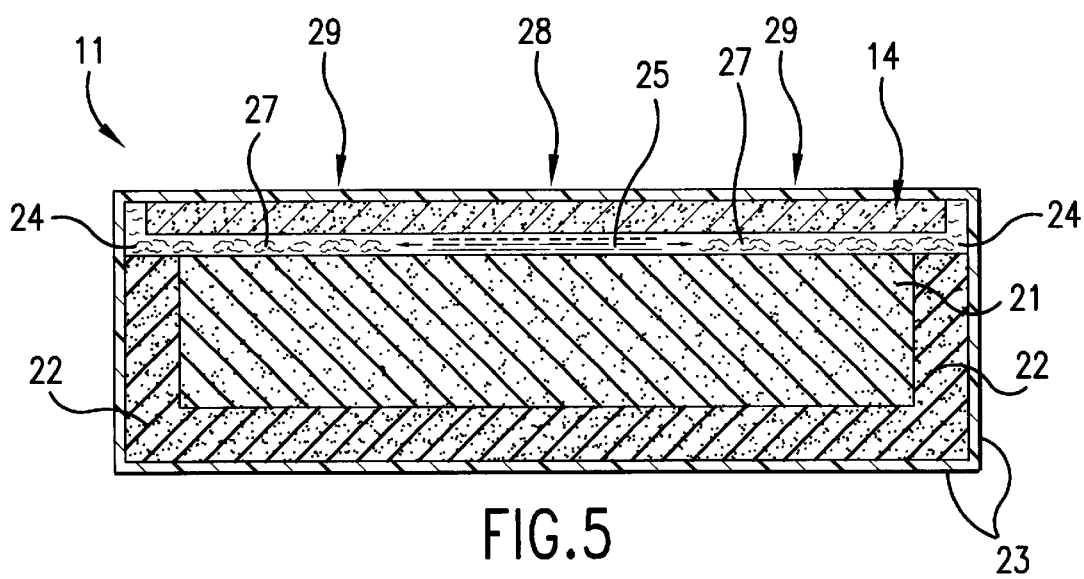
FIG. 5 is a cross-sectional view of an alternate embodiment of a support surface according to the present invention.

FIGS. 4 and 5 illustrate preferred alternate constructions, or embodiments, of the mattress 11 herein. In FIG. 4, the thermal layer 14 does not extend the width of the mattress, as it does on FIG. 3. The mattress 11 includes high conductivity material edge inserts 30 along the right and left sides of the thermal layer 14 of the mattress 11. The edges of the base support layer 22 extend up on the left and right sides of the mattress, with the scow-shaped softer compression support layer 21 in the middle. Above the support layers 21, 22 a cross-section of a heat tube 24 is shown in FIG. 4. The liquid refrigerant liquid 25 at the center of the heat tube 24 is shown in vapor form 27 in the cool zone 29 on either side of the central warm zone 28, as it would be if there was a body on the mattress 11. The uppermost layer is a cloth textile layer 23A, which serves to wick moisture away from the body. Keeping the body dry is known to be helpful in avoiding bedsore formation.

In FIG. 5, the base support layer 22 extends upward in columns at the right and left edges of the mattress 11, and the lower ILD (indentor load deflection) central compression layer 21 is squared off at the bottom. The heat tube 24 extends in an upward direction at the right and left sides of the mattress, which enhances condensation and flow return at these ends. The liquid refrigerant liquid 25 at the center of the heat tube 24 is shown in vapor form 27 in the cool zone 29 on either side of the central warm zone 28, as it would be if there was a body on the mattress 11. It is less comfortable for the user to lie on one side of the bed, where the stiffer base support layer 21 is. The thermal layer 14, with its carrier 16 and phase change material 15, extends between the two ends of the heat tubes 24, as shown in FIG. 5.

Figure 6:
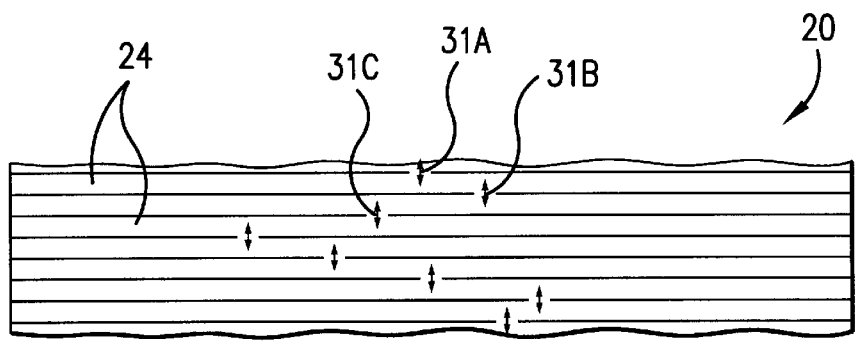
FIG. 6 is a schematic top view of an alternate embodiment of a support surface according to the present invention, showing flow between heat tubes.

While FIGS. 4 and 5 show latitudinal cross-sections of the mattresses, FIG. 6 is a portion of a longitudinal cross-section taken along the heat tube layer 20, as viewed from the top. The heat tube layer 20 extends across the mattress 11. The right and left sides of the mattress 11 are shown at the right and left sides of FIG. 6. As illustrated in FIG. 6, each set of two adjacent heat tubes 24 has an opening 31 at one point between the two tubes, so that liquid or gas refrigerant 25, 27 can flow between the two heat tubes 24. The openings are at different locations for each set of heat tubes, though, as indicated by 31A and 31B and 31C. This allows the exchange of liquid and vapor between heat tubes. In FIG. 6, the vapor flows back and forth, as indicated by the arrows.

Figure 8:
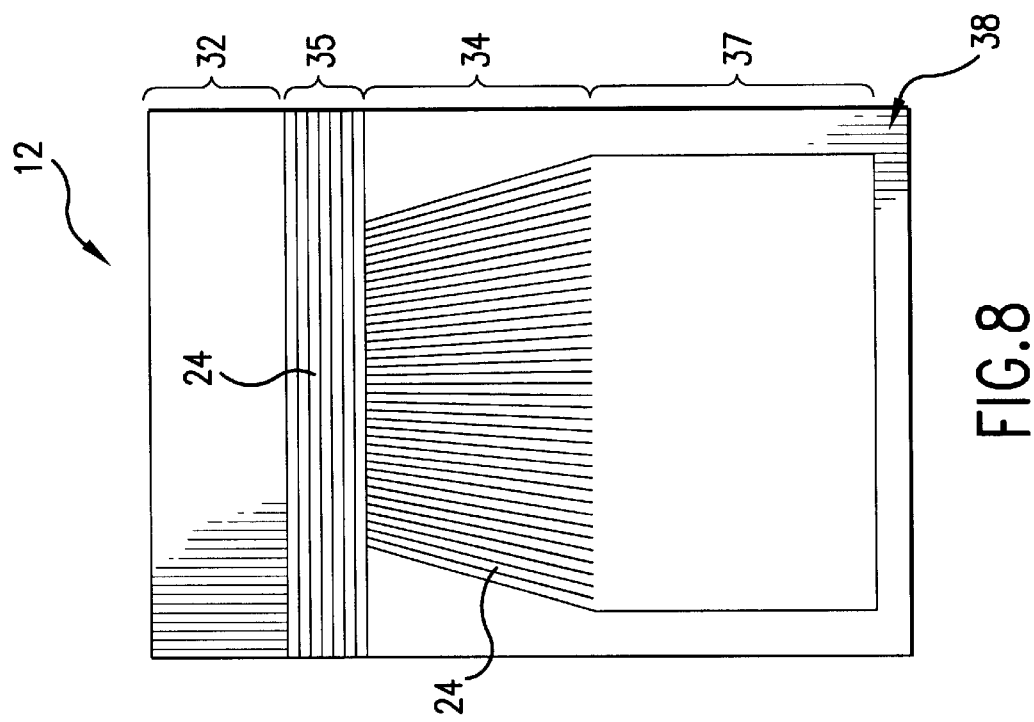
FIG. 8 is a top plan view of an alternate embodiment of a support pad according to the present invention.
Figure 7:
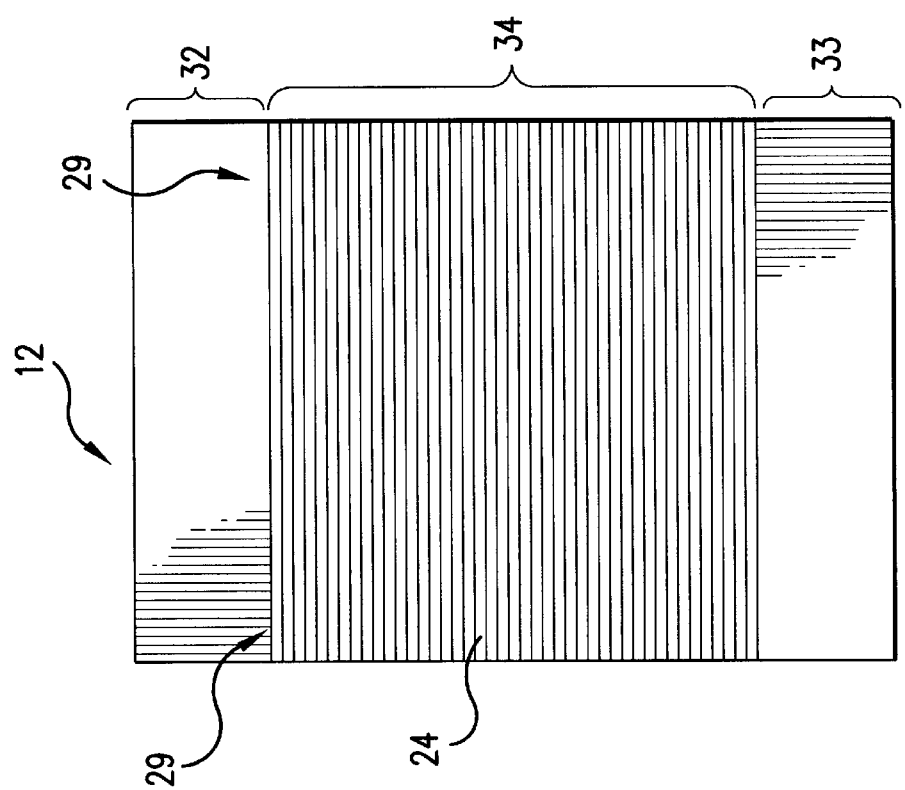
FIG. 7 is a top plan view of an alternate embodiment of a support pad according to the present invention.

FIGS. 7 and 8 show alternate embodiments of a support surface pad 12 herein. The heat tube layer 20 is shown in different arrangements for achieving different effects. The arrangement chosen by the consumer user could depend upon the problem that the user was having, and the particular cooling areas desired. The heat tube layer 20 can be used with or without a thermal layer above or below it. The heat tube layer 20 is preferably made from a large, thin bladder with parallel and/or perpendicular RF welds dividing it into heat tubes 24. It can resemble the air mattresses used in pools. Each heat tube 24 is preferably cylindrical in shape, but can be rectangular or disc-shaped, for example, depending on where the welds are placed. The bladder is made from a soft, flexible, durable material that is inpermeable to the selected refrigerant, or refrigerants, in both liquid and gas phases. The bladder holds a relatively small amount of the refrigerant 25, which can preferably pass back and forth between the heat tubes 24, as shown in FIG. 6.

In FIG. 7, a head area 32 and foot area 33 of the support pad 12, or mattress, have parallel, vertically oriented heat tubes 24. The main body area 34 has parallel, horizontally oriented heat tubes 24 extending across the width of the bed. In contrast with the vertically oriented heat tubes in the head and foot areas, the horizontally oriented heat tubes 24 in the main body area 34 channel heat away from the vertically oriented body to the cool zones 29 to the left and right of the body.

In FIG. 8, the head area 32 of the support pad 12, or mattress, also has parallel, vertically oriented heat tubes 24. A shoulder area 35 under the head area 32 has parallel, horizontally oriented heat tubes 24 for channeling heat away from the shoulder area of the body toward the cool zone 29. If the user is of average height, his or her torso lies over a torso area 36 with heat tubes 24 that angle outward from the top of the area to the bottom of the area. Due to the orientation of the torso area heat tubes, heat is not distributed away from the torso. The leg area 37 of this embodiment does not contain heat tubes. A user's legs (distal), which would rest on the leg area 37, generally have a lower body temperature than the head and torso (proximal) of the body. The peripheral lower area 38 of the bed in FIG. 8 includes vertically oriented heat tubes for channeling heat down to the user's feet, which would likely rest in this area of the mattress 11.

The heat tube areas 32, 34, 35, 36 shown in FIGS. 7 and 8 are somewhat large so that the support pad 12 accommodates a range of users who are relatively average in height. The support pad 12 or mattress 11 can be customized for very tall or short users.

The support surface can also be used simply for delaying warming of the surface of the skin in contact with the support surface, and does not include the heat tube layer or the two lower support layers. A support surface pad herein includes:

(a) phase change material 15 having a melting point of between about 18 and 32 degrees Centigrade;

(b) a gel or viscous fluid carrier 16 in which the phase change material 15 is substantially evenly distributed; and (c) a fluid-impermeable, conformable envelope 17 surrounding the phase change material and the carrier.

Examples of such pads are seat pads, mattress overlay pads, positioning pads, etc. If the support surface pad is a seat cushion or the like, a thin layer of insulation over the upper surface of the pad is preferred. The insulation layer helps to prolong the effect of the phase change material. A thin seat pad could be used, for example, on a truck or taxi driver's seat to slow heating of the driver's back during a long drive. The support pad 12 would keep the driver's back cooler than it would have been without the pad. It could, of course, be used on other seats as well. The present invention maintains its cooling effect for a time below the "perspiration threshold" of 32 to 33 degrees Centigrade, the temperature above which the skin perspiration rate increases markedly.

The phase change material is substantially evenly distributed in a carrier 16 which is a gel, such as a urethane gel or a viscous fluid. By "viscous fluid" is meant a fluid with an absolute viscosity between about five and about 100,000 centipoise, most preferably between about five and about 10,000 centipoise. As phase change material is added, the carrier stiffens somewhat; for support surfaces that need to be soft, carriers with a lower viscosity are preferable. Urethane gels, silicone fluids, and mineral oils are among the suitable carriers in this regard. It is also believed that inexpensive oils, such as vegetable oil, olive oil, or peanut oil, may also be employed herein, so long as they have a suitably high viscosity and a preservative is included. The carrier and phase change material are both preferably non-toxic, and inter-mixable. The phase change material must maintain distribution within the carrier through a plurality of hot/cold cycles. The viscous, conformable fluid carrier herein should not foster bacterial or fungal growth when confined in the air- and fluid-impermeable envelope.

It is believed that a viscous fluid is optimal herein for maintaining phase change material distribution and for even cooling. Polydimethylsiloxane fluid and dimethicone fluid are more preferred for use herein.

Viscosity is a significant property of the material that is selected to carry the phase change material because it determines, in large part, the degree of pad deformation that will occur in response to a given force. Viscosity is basically the resistance to change of form exhibited by a fluid. It is a measure of internal friction and is measured as the amount of tangential force exerted by one layer of fluid upon an adjacent layer as it driven across it at a given velocity. The viscosity of the fluid carrier affects the support pad's conformability and cushioning characteristics for mattress and seating applications, as well as for other applications herein. It also affects the tendency for a dispersed powder to maintain its dispersion. For this reason, very low viscosity fluids, such as water and alcohol, are believed not to be desirable as carriers herein.

As shown in FIG. 1, the PCM-containing carrier is contained within the thin, fluid-impermeable, conformable covering, or envelope 17, which surrounds the PCM-containing gel or viscous fluid carrier 16. The concentration of phase change material to carrier by weight is preferably between about 1:5 and 5:1, more preferably between about 2:1 and 1:2, most preferably 1:1. This ratio has generally been found to be of importance because, for most types of phase change materials and carriers, the more phase change material that is added to the carrier beyond a certain minimal level, the stiffer and firmer the mixture becomes. Although in general more phase change material means longer lasting cooling cycles, too much phase change material results in an unacceptably hard support surface.

The envelope 21 is preferably made of a urethane film with a thickness of between about 0.003 and 0.018 inch, most preferably between about 0.03 and about 0.1 inch. The envelope 17 is preferably rectangular in shape and the width and length of the mattress or other surface it is intended to cover. The envelope 17 may include internal divisions. It may, for example, be quilted, with a small amount of phase change material and carrier in each quilt square.

Figure 9:
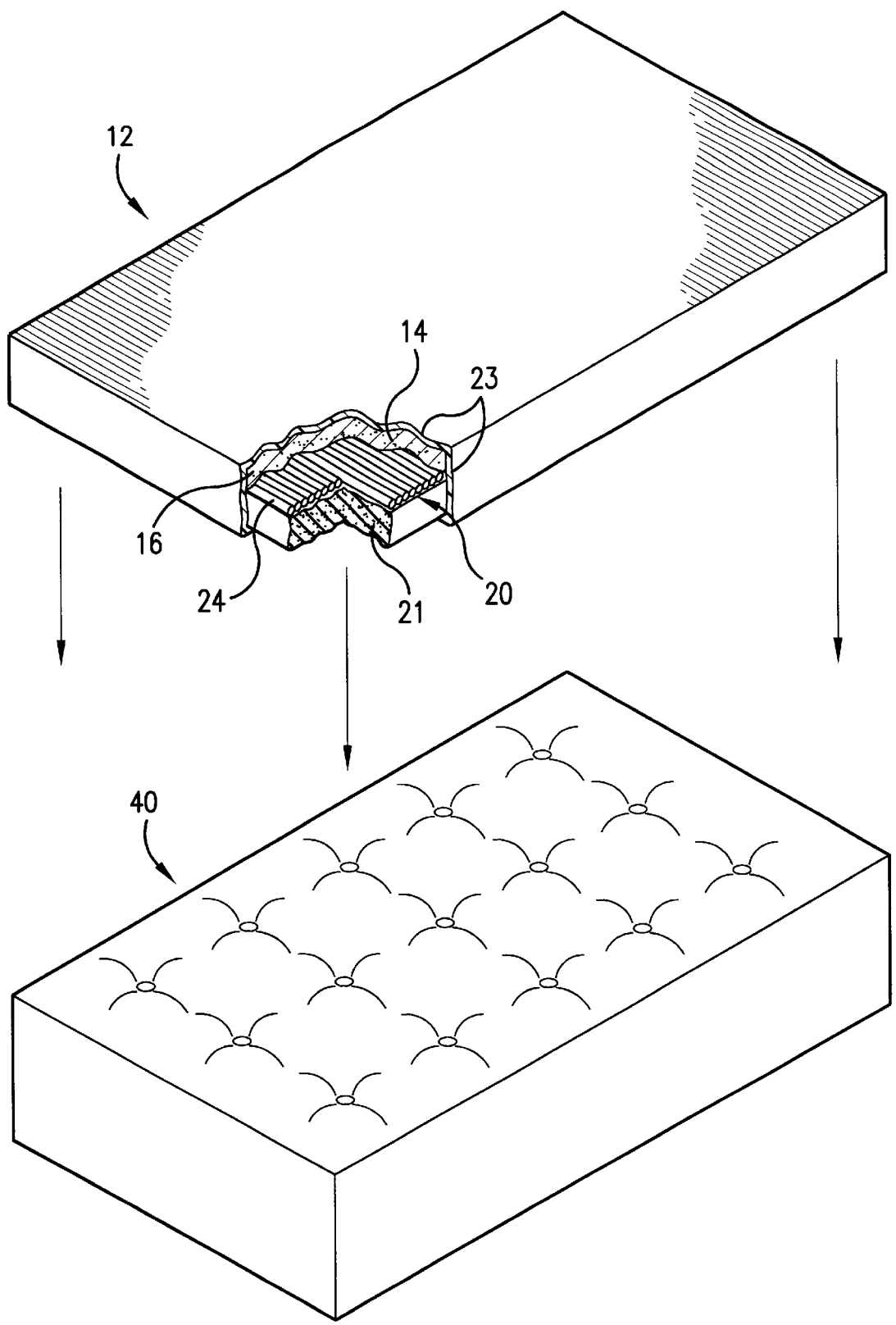
FIG. 9 is a perspective view of a support pad according to the present invention, showing intended use.
Figure 10:
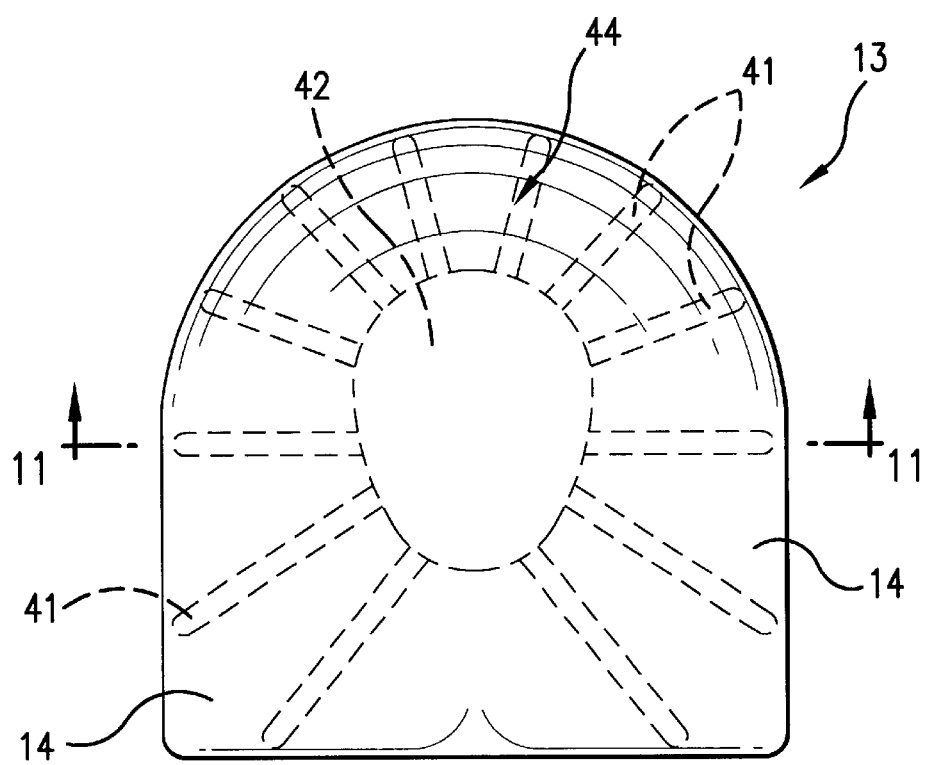
FIG. 10 is a top plan view of a seat cushion according to the present invention.

In a preferred embodiment, the gel carrier is silicone fluid, and the ratio by weight of silicone fluid: PCM is between 1:5 and 5:1, preferably about 1:1. Also, in a preferred embodiment, the support surface is a wheelchair seat cushion, a panel that is insertable into a mattress, or a cooling overlay pad FIG. 9 shows a mattress pad 12, which can be placed on the top of any conventional mattress 40, or used by itself, for example, under a sleeping bag on a camping trip. An upper thermal layer 14 includes phase change material 15 distributed throughout a carrier 16. A heat tube layer 20 under the thermal layer 14 includes parallel, adjacent heat tubes 24 oriented (horizontally) from one side of the support pad 12 to the other. In this embodiment, the cylindrical, same-sized heat tubes 24 preferably have a diameter of about ½ inch. A compression support layer 21 under the heat tube layer 20 provides some support for the body and the heat tube layer. These three layers are enclosed in an outer covering 23, such as a durable fabric.

The support pad 12 does not require a base support layer. When the support pad is used on a conventional mattress, the mattress provides support for the body. The support pad is useful, for example, in a hospital ward, operating room, or recovery room, or wherever a mattress 11 is not available and temporary cooling relief is desired. It can be used under a febrile patient, for example, or one who is about to undergo a CAT scan or X-ray. The surface of the support pad 12 is washable, but if the pad rips or is irreparably soiled, it is inexpensive enough to be discarded.

Figure 11:
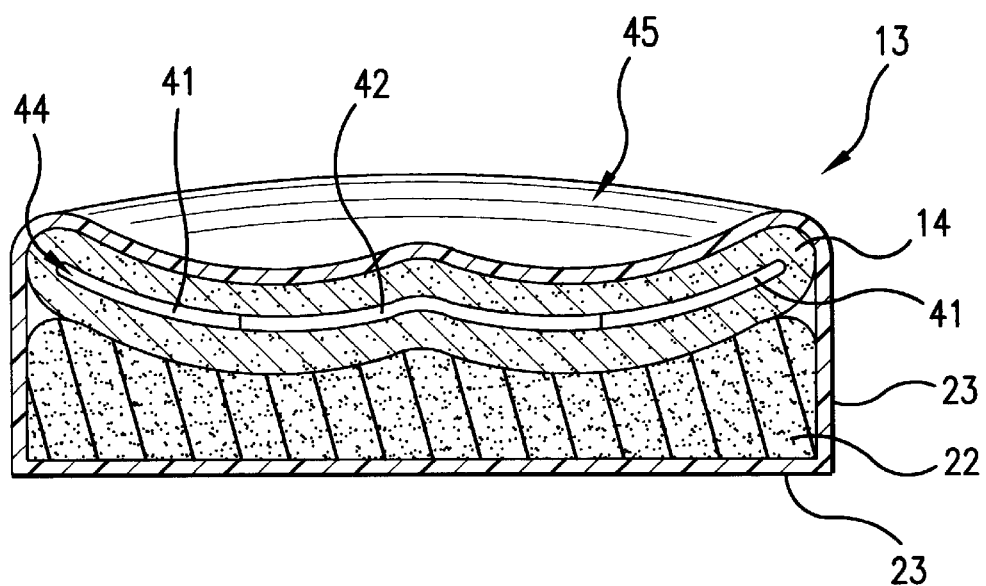
FIG. 11 is a cross-sectional view of the seat cushion of FIG. 10, taken along line 11—11.
Figure 12:
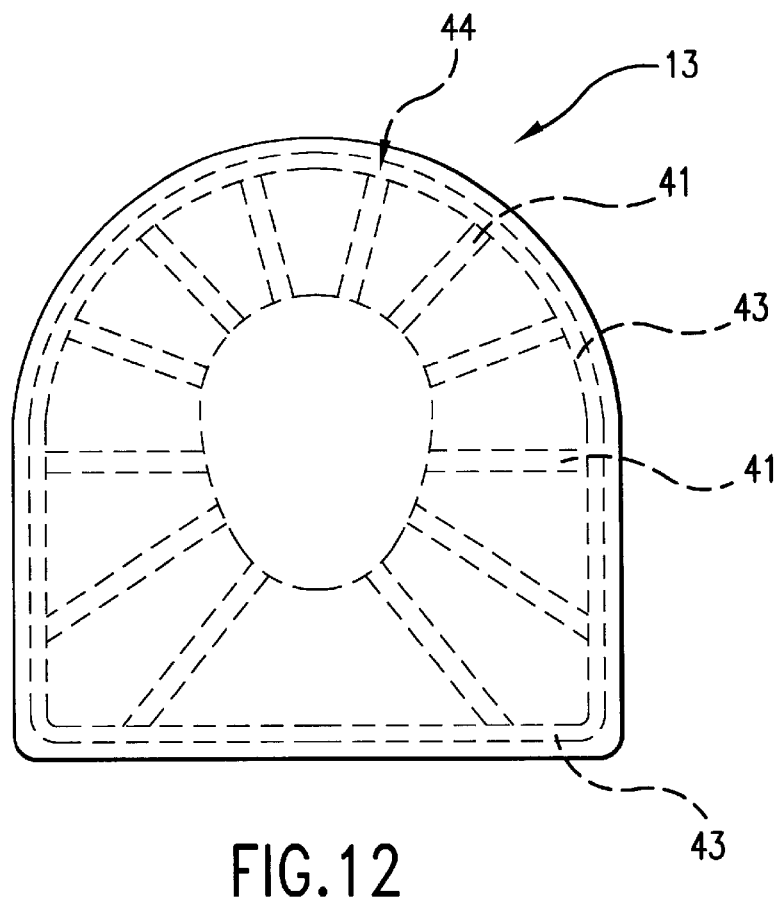
FIG. 12 is a top plan view of a seat cushion according to the present invention.
Figure 13:
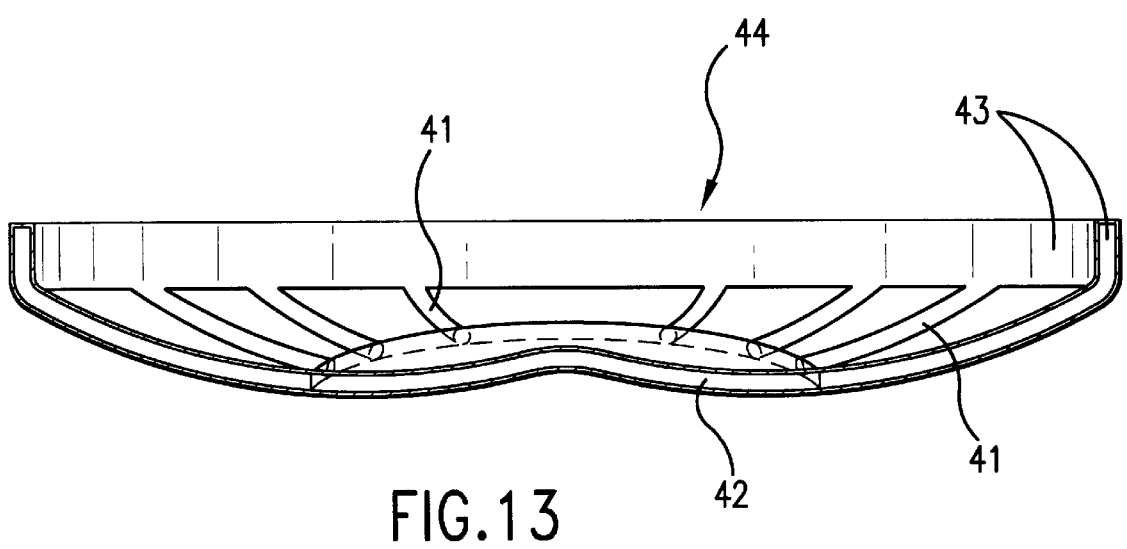
FIG. 13 is a cross-sectional view of the seat cushion of FIG. 12, taken along line 13—13.

FIGS. 10 through 13 show two embodiments of a seat cushion 13 from the top (FIGS. 10 and 12) and in cross-section (FIGS. 11 and 13). In the embodiment shown in FIGS. 10 and 11, heat tubes 41 radiate outward from a central bladder 42. The heat tube system includes the bladder 42 and radiating heat tubes 41. The cross-section (FIG. 11) of the seat cushion 13 shows the bladder 42 with a heat tube 41 extending from each side of the bladder 42. The bladder 42 is generally lower in elevation than the ends of the heat tubes 41. Also, the upper surface of the seat cushion 13 is also contoured for comfort. The heat tube system is sandwiched within the thermal layer 14. This is supported by a base support layer 22, and may include a compression support layer. The seat cushion 13 is enclosed by an outer covering 23. When a person sits on the seat cushion 13, the central bladder 42 heats up, which causes refrigerant liquid 25 in the bladder 42 to move to the gaseous state 27. The gas 27, or vapor, rises to the cooler, higher ends of the heat tubes 41, where it condenses and flows by gravity back to the central bladder. The warming/cooling heat tube cycle then repeats itself within the heat tube system 44. At the same time, the phase change material within microcapsules distributed within the carrier in the thermal layer 14 is heating in a controlled fashion so as to prolong the cooling effect. The thermal layer effect and the heat tube effect are additive and result in a cushion that is cool and comfortable.

In the embodiment of FIGS. 12 and 13, the heat tubes 41 radiate out to a peripheral ring 43 within the periphery of the cushion 13. This embodiment does not include a thermal layer. In FIGS. 12 and 13, the heat tubes connect the bladder 42 to the peripheral ring, so liquid and gas refrigerant 25, 27 can flow within the heat tube system 44. The heat tube system 44 includes the bladder 42, heat tubes 41, and peripheral ring 43.

FIG. 12 shows contouring of the heat tube system 44 as viewed from the side. When a person sits on the seat cushion 13, the central bladder 42 heats up, which causes refrigerant liquid 25 in the bladder 42 to move to the gaseous state 27. The gas 27, or vapor, rises to the cooler periphery of the seat cushion, where it condenses and flows by gravity back to the central bladder, which is lower in elevation than the heat tubes 41. Contouring of the upper surface 45 of the seat cushion 13 also makes it more comfortable to sit on. This seat cushion 13 is particularly useful as a wheelchair pad. The cushion 13 could alternatively be a dog bed which would be helpful, for example, for an aging, infirm dog.

It has been found herein that one problem with some of the heat tube materials is that they crackle when a user sits or lies on them. In all embodiments herein, the heat tubes 41 may be surrounded by a second gel or viscous fluid, such as a silicone gel, and enclosed by a second envelope. The fluid/gel muffles the distracting crackling sound. This second envelope preferably lies side by side with the first, PCM-containing envelope 17. Another alternative is to include the heat tubes 41 in the PCM-containing envelope 17. The carrier 16 around the heat tubes 41 in the envelope 17 then muffles the crackling sound.

Figure 14:
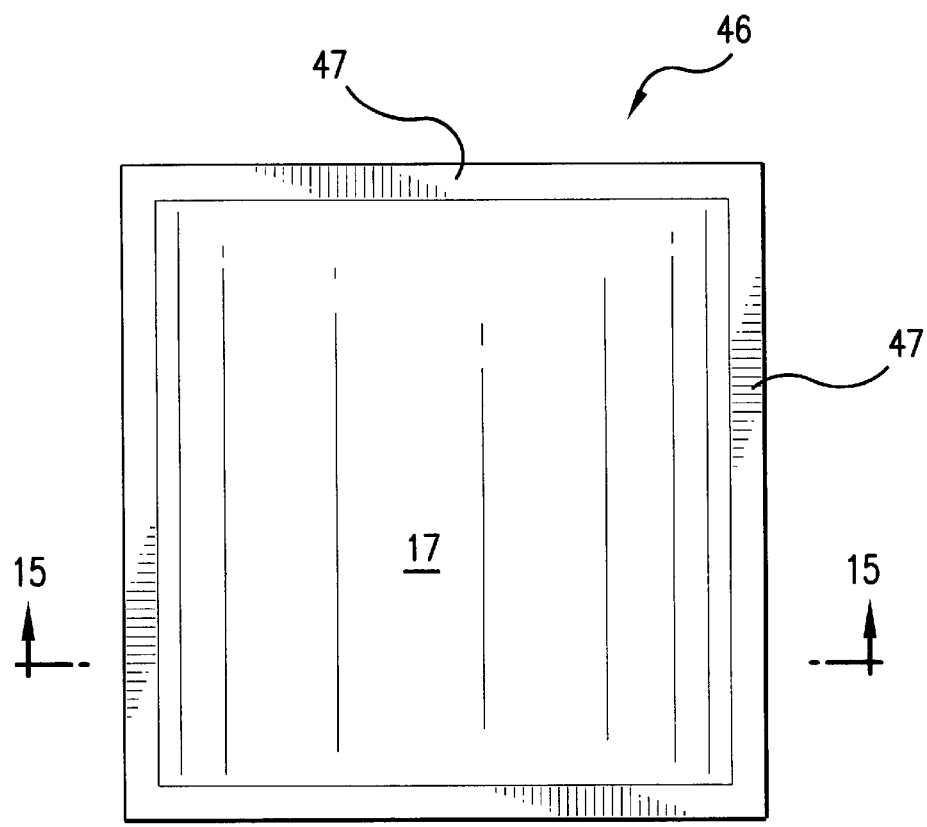
FIG. 14 is a top plan view of an envelope of a seat cushion according to the present invention.
Figure 15:
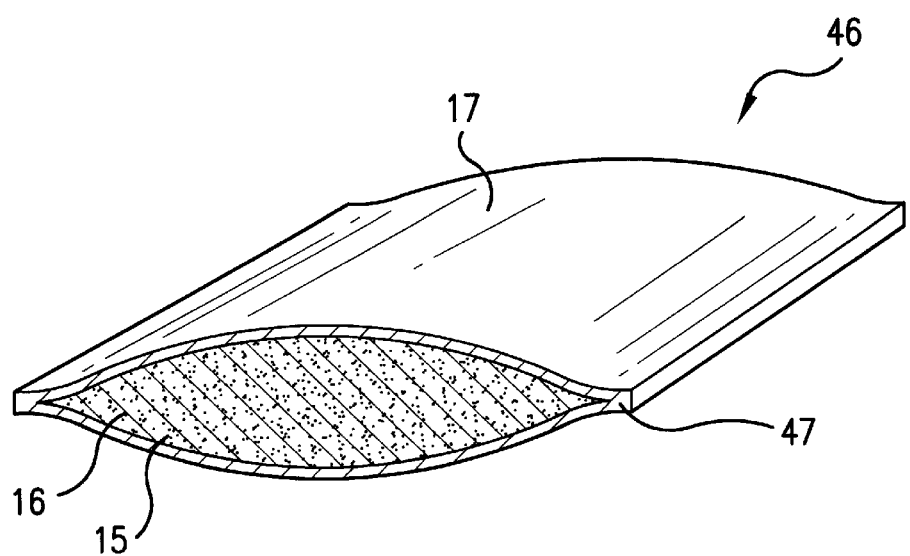
FIG. 15 is a cross-sectional view of the envelope of FIG. 14, taken along line 15—15.

Referring now to FIGS. 14 and 15, an operating room ("OR") pad 46 includes a urethane film envelope 17 holding carrier 16 in which phase change materials 15 have been distributed. The fluidic PCM/carrier contents are enclosed by the flexible envelope 17, which is then preferably heat sealed along the edges 47. The top of the operating room pad 46, as shown in FIG. 14, is the same as the bottom. FIG. 15 shows the inside of the pad 46. In a preferred embodiment, the envelope 17 is urethane film, the carrier 16 is a silicone fluid, and the phase change material 15 is an C16–19 alkane mixture encapsulated into microcapsules with a diameter between about one and 100 microns. These operating room pads 46 can be used, for example, to pack around a patient undergoing a medical procedure that requires cooling of a limb or any other part of the body. The operating room pads 46 are similar in appearance to overlay pads.

Figure 16:
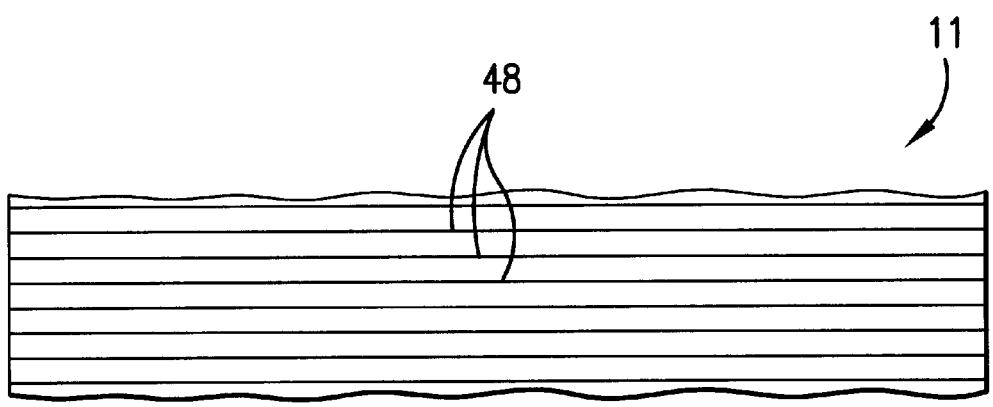
FIG. 16 is a schematic top view of an alternate embodiment of a support surface according to the present invention.

In a section of an alternate embodiment shown in FIG. 16, fine copper wires 48, or other conductive materials, such as a copper layer or high conductivity polymers, are embedded in, or beneath and at least partially adjacent to, the thermal layer 14 in order to enhance thermal conductivity in a given direction to the cool zone. In the top plan view of FIG. 16, a number of copper wires 48 are shown parallel to one another in a horizontally oriented direction within the carrier 16, from one side of the mattress 11 to the other. This embodiment does not include a heat tube layer.

From the foregoing it can be realized that the described device of the present invention may be easily and conveniently utilized as a cooling support surface. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A clinical support surface pad for reducing the incidence and promoting the healing of bedsores, the support surface pad comprising:
   (a) phase change material having a melting point of between about 18 and 32 degrees Centigrade;
   (b) a gel or viscous fluid carrier in which the phase change material is substantially evenly distributed; and
   (c) a fluid-impermeable, conformable envelope surrounding the phase change material and the carrier;
   wherein the carrier is urethane gel.

2. A support surface pad according to claim 1, further comprising a copper layer beneath and at least partially adjacent to the envelope.

3. A clinical support surface pad for reducing the incidence and promoting the healing of bedsores, the support surface pad comprising:
   (a) phase change material having a melting point of between about 18 and 32 degrees Centigrade;
   (b) a gel or viscous fluid carrier in which the phase change material is substantially evenly distributed;
   (c) a fluid-impermeable, conformable envelope surrounding the phase change material and the carrier; and
   (d) at least one conformable compression support layer beneath and adjacent to the envelope.

4. A support surface pad according to claim 3, wherein the phase change materials are microencapsulated in a protective coating.

5. A support surface pad according to claim 3, which does not comprise a power source or microprocessor.

6. A support surface pad according to claim 5, wherein the carrier is an oil.

7. A support surface pad according to claim 3, wherein the envelope is a urethane film.

8. A support surface pad according to claim 7, wherein the phase change material is a C16 to C19 alkane, or a combination thereof.

9. A support surface pad according to claim 8, wherein the phase change material is microencapsulated with a polymer coating, forming generally spherical PCM/polymer microcapsules which range in diameter between about one and about 100 microns.

10. A support surface pad according to claim 9, wherein the carrier is a silicone fluid.

11. A support surface pad according to claim 10, wherein the envelope is a urethane film.

12. A support surface pad according to claim 11, wherein the support surface pad is a seat cushion, a panel that is insertable into a mattress, or a cooling overlay pad.

13. A support surface pad according to claim 3, wherein the carrier is urethane gel.

14. A clinical support surface for reducing the incidence and promoting the healing of bedsores, the support surface comprising:
   (a) at least one thermal layer comprising: a phase change material having a melting point of between about 18 and 32 degrees Centigrade; a gel or viscous fluid carrier in which the phase change material is substantially evenly distributed; and a fluid-impermeable, conformable envelope surrounding the phase change material and the gel or fluid carrier;
   (b) at least one conformable compression support layer beneath and adjacent to the thermal layer;
   (c) at least one conformable base support layer beneath and adjacent to the compression layer, the base support layer having a higher indentor load deflection (ILD) than the compression layer;
   wherein the layers are joined within an outer covering.

15. A support surface pad according to claim 14, further comprising a plurality of copper wires embedded in the thermal layer.

16. A support surface according to claim 14, further comprising a heat tube layer, comprising at least two adjacent heat tubes, at least one of the heat tubes containing a refrigerant liquid with a boiling point between about 23 and about 33 degrees Centigrade.

17. A support surface according to claim 16, further comprising a net suspended within at least one of the heat tubes.

18. A support surface according to claim 17, wherein the support layers are foam, and the support surface is a mattress.

19. A support surface according to claim 14, wherein the phase change materials are microencapsulated in a protective coating.

20. A support surface according to claim 19, which does not comprise a power source or microprocessor.

21. A support surface according to claim 19, wherein the envelope is a urethane film.

22. A support surface according to claim 21, wherein the phase change material is encapsulated with polymer, forming generally spherical PCM/polymer microcapsules, which range in diameter between about one and about 100 microns.

23. A support surface according to claim 22, wherein the carrier is polydimethylsiloxane fluid.

24. A support surface according to claim 14, wherein the phase change material is a C16 to C19 alkane, or a combination thereof.

25. A support surface according to claim 24, wherein the PCM is microencapsulated by a polymer coating.

26. A support surface according to claim 25, wherein the carrier is urethane gel.

27. A support surface pad according to claim 26, wherein the carrier is a mineral oil.

28. A support surface according to claim 26, wherein the ratio by weight of fluid carrier to phase change material is between about 1:5 and 5:1.

29. A support surface according to claim 14, further comprising at least two adjacent heat tubes within the envelope, at least one of the heat tubes containing a refrigerant liquid with a boiling point between about 23 and about 33 degrees Centigrade.

30. A support surface according to claim 29, wherein the refrigerant liquid is pentafluoropropane, or fluorochemical liquid.

31. A support surface for comfort or reducing the incidence and promoting the healing of bedsores, the support surface comprising:

(a) at least one heat tube layer comprising at least two adjacent heat tubes, at least one of the heat tubes containing a refrigerant liquid, the refrigerant liquid having a boiling point between about 80 and about 85 degrees Fahrenheit;

(b) at least one conformable compression support layer beneath and adjacent to the heat tube layer; and (c) at least one conformable base support layer beneath and adjacent to the compression layer, the base support layer having a higher indentor load deflection (ILD) than the compression layer;

wherein the layers are joined within an outer covering, and the support surface does not comprise a manually operated temperature control unit.

* * * * *